United States Patent
Wohlfart et al.

(10) Patent No.: US 6,812,253 B2
(45) Date of Patent: Nov. 2, 2004

(54) 4-FLUORO-N-INDAN-2-YL BENZAMIDE AND ITS USE AS A PHARMACEUTICAL

(75) Inventors: Paulus Wohlfart, Bensheim (DE); Teri Suzuki, Tucson, AZ (US); Ramalinga M. Dharanipragada, Belle Meade, NJ (US); Alena Safarova, Tucson, AZ (US); Armin Walser, Tucson, AZ (US); Hartmut Strobel, Liederbach (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/623,775

(22) Filed: Jul. 22, 2003

(65) Prior Publication Data

US 2004/0019114 A1 Jan. 29, 2004

Related U.S. Application Data

(63) Continuation of application No. 10/073,330, filed on Feb. 13, 2002, now Pat. No. 6,617,359.

(30) Foreign Application Priority Data

Feb. 13, 2001 (EP) .............................. 01102852

(51) Int. Cl.$^7$ ............................ A61K 31/165
(52) U.S. Cl. .................................... 514/617
(58) Field of Search ......................... 514/617

(56) References Cited

U.S. PATENT DOCUMENTS 6,617,359 B2 * 9/2003 Wohlfart et al. ............ 514/617

FOREIGN PATENT DOCUMENTS

| WO | WO 99/47153 A3 | 9/1999 |
| WO | WO 99/47153 A2 | 9/1999 |
| WO | WO 00/03746 | 1/2000 |
| WO | WO 00/51970 | 9/2000 |

OTHER PUBLICATIONS

Matthias Endres et al., Stroke Protection by 3-hydroxy-3-methylgulutaryl (HMG)-CoA reductase inhibitors mediated by endothelial nitric oxide synthase, Proc. Natl. Acad. Sci. USA, Jul. 1998, vol. 95, pp. 8880–8885.

Huige Li et al., Activation of Protein Kinase Ca and/or $\epsilon$ Enhances Transcription of the Human Endothelial Nitric Oxide Synthase Gene, Molecular Pharmacology (1998) 53:630–637.

M. F. McCarty, Up-regulation of endothelial nitric oxide activity as a central strategy for prevention of ischemic stroke —Just say NO to stroke!, Medical Hypotheses (2000) 55(5), 386–403.

Masao Moroi et al., Interaction of Genetic Deficiency of Endothelial Nitric Oxide, Gender, and Pregnancy in Vascular Response to Injury in Mice, The Journal of Clinical Investigation, Mar. 1998, vol. 101, No. 6, 1225–1232.

Masafumi Nakayama et al., $T^{786} \rightarrow C$ Mutation in the 5'–Flanking Region of the Endothelial Nitric Oxide Synthase Gene Is Associated WIth Coronary Spasm, Clinical Investigation and Reports (1999) 2864–2870.

William C. Sessa et al., Chronic Exercise in Dogs Increases Coronary Vascular Nitric Oxide Production and Endothelial Cell Nitric Oxide Synthase Gene Expression, Circulation Research, 1994, vol. 74, No. 2, 349–353.

Olivier Varenne et al., Percutaneous Gene Therapy Using Recombinant Adenoviruses Encoding Human Herpes Simplex Virus Thymidine Kinase, Human PAI–1, and Human NOS3 in Balloon–Injured Porcine Coronary Arteries, Human Gene Therapy (Jun. 10, 2000) 11:1329–1339.

* cited by examiner

*Primary Examiner*—Raymond J. Henley, III
(74) *Attorney, Agent, or Firm*—Finnegan, Henderson, Farabow, Garrett and Dunner, L.L.P.

(57) ABSTRACT

The present invention relates to the method of stimulating the expression of endothelial NO-synthase in a mammal, which method comprises administering a physiologically active amount of 4-fluoro-N-indan-2-yl benzamide according to the formula (I)

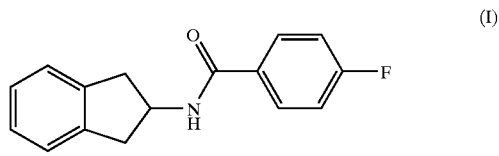

(I)

to the said mammal. Compound (I) can be used for the therapy and prophylaxis of cardiovascular diseases like stable and unstable angina pectoris, Prinzmetal angina (spasm), acute coronary syndrome, heart failure, myocardial infarction, stroke, thrombosis, peripheral artery occlusive disease PAOD, atherosclerosis, restenosis, endothelial damage after PTCA, essential hypertension, pulmonary hypertension, secondary hypertension, renovascular chronic glomerulonephritis, erectile dysfunction, ventricular arrhythmia, and the lowering of cardiovascular risk of postmenopausal women or after intake of contraceptives, the therapy and prophylaxis of diabetes and diabetes complications (nephropathy, retinopathy), angiogenesis, asthma bronchiale, chronic renal failure, cirrhosis of the liver, restricted memory performance or a restricted ability to learn.

18 Claims, No Drawings

4-FLUORO-N-INDAN-2-YL BENZAMIDE AND ITS USE AS A PHARMACEUTICAL

This is a continuation of application Ser. No. 10/073,330, filed Feb. 13, 2002, which was issued as U.S. Pat. No. 6,617,359 B2 on Sep. 9, 2003, and claims benefit under 35 U.S.C. § 119 of European Patent Application No. 01102852.9, filed Feb. 13, 2001, all of which are incorporated by reference herein.

The present invention relates to 4-fluoro-N-indan-2-yl benzamide of the formula (I) and its use as pharmaceutical agent.

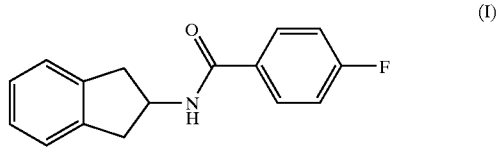

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium, and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349–353) were able by means of exercise training and the increase in shear stress associated therewith to obtain a marked increase in eNOS.

Whether regulation at the post-transcriptional level is relevant in vivo, is not unambiguously proved. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides the lipid lowering, also in part to an increase in eNOS expression in vivo (Endres et al., Proc. Natl. Acad. Sci. USA 95 (1998) 8880–8885). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864–2870).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329).

Some low molecular weight compounds which, in cell cultures, may lead to a direct effect on eNOS transcription and expression are disclosed in the literature. The statins which have already been mentioned are, however, the only substances for which it has been possible to date to show such an increase in eNOS in vivo as a side effect. In view of the known range of side effects of this class of substances, however, it is unclear how far this effect is present in a toxicologically unproblematic dose.

Liao et al. claim in WO 99/47153 and WO 00/03746 the use of rhoGTPase inhibitors and agents which influence the organization of the actin cytoskeleton for increasing eNOS in endothelial cells and for the therapy of various disorders such as, for example, strokes or pulmonary hypertension, without, however, indicating a specific way of achieving this.

Thus, there exists a strong need for a medicament which upregulates eNOS-expression in endothelial cells. The object of the present invention is to provide a compound showing this ability.

This object is attained by the use of 4-fluoro-N-indan-2-yl benzamide according to the formula (I)

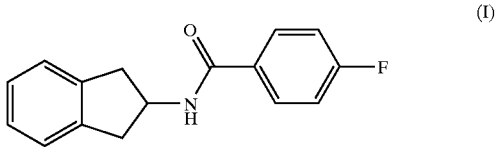

for the manufacture of a medicament for the stimulation of the expression of endothelial NO synthase.

This object is also attained by a pharmaceutical preparation for the stimulation of the expression of endothelial NO synthase comprising an effective dose of 4-fluoro-N-indan-2-yl benzamide and a pharmaceutically acceptable carrier.

The present invention furthermore includes the use of all solvates of the compound according to formula (I), for example, hydrates, adducts with alcohols, active metabolites of the compound of formula (I), and also derivatives and prodrugs of the compound of formula (I) which contain physiologically tolerable and cleavable groups, for example, esters, amides and compounds in which the N—H group depicted in formula (I) is replaced with a N-alkyl group, such as N-methyl, or with a N-acyl group, such as N-acetyl or N-argininyl, including pharmaceutically acceptable salts formed on functional groups present in the N-acyl group.

WO 00/51970 discloses the manufacture and use of 4-fluoro-N-indan-2-yl benzamide as a medicament. The compound possesses strong potentiation of the cholinergic activity, and is useful for the treatment and/or prevention of disorders in the central nervous system for mammals, and more particularly of amnesia, dementia, e.g. senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, and the like. The compound is expected to be useful as a therapeutic and/or preventive agent for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism. WO 00/51970 does not disclose or suggest the use of 4-fluoro-N-indan-2-yl benzamide for the upregulation of the expression of endothelical NO-synthase, in particular for the treatment of cardiovascular diseases, stable or unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, restenosis, endothelial damage after PTCA, hypertension, essential hypertension, pulmonary hypertension, secondary hypertension, renovascular hypertension, chronic glomerulonephritis, erectile dysfunction, ventricular arrhythmia, diabetes or diabetes complications, nephropathy, retinopathy, angiogenesis, asthma bronchiale, chronic renal failure, cirrhosis of the liver, osteoporosis, restricted memory performance, a restricted ability to learn, or the lowering of cardiovascular risk of postmenopausal women or after intake of contraceptives.

The compound according to formula (I) can be prepared starting from 2-indanylamine which is known in the literature. 2-Indanyl amine can be reacted, in the form of the free base or a salt thereof, with 4-fluorobenzoylchloride in the presence of a base like, for example, triethylamine. The reaction is generally carried out in a solvent like dichloromethane, tetrahydrofuran, toluene or dioxane, and preferably at room temperature. Alternatively, the compound according to the formula (I) is obtained by a coupling reaction of the said 2-indanyl amine with 4-fluorobenzoic acid, in the presence of a base like, for example, diisopropylethylamine, and the use of an appropriate coupling reagent like, for example, carbodiimides, HATU or TOTU.

Further reactions for the synthesis of the compound according to the formula (I) are apparent to or well-known to the skilled person and can be carried out under standard conditions according to or analogously to procedures described in the literature, for example in Houben-Weyl, Methoden der Organischen Chemie (Methods of Organic Chemistry), Thieme-Veriag, Stuttgart, or Organic Reactions, John Wiley & Sons, New York. If desired, the compound of the formula (I) can be purified by customary purification procedures, for example by recrystallization or chromatography. The starting compounds for the preparation of the compound of the formula (I) are commercially available or can be prepared according to or analogously to literature procedures.

The compound according to the formula (I) can be used to upregulate the expression of the endothelial NO synthase and is a useful pharmaceutical compound for the treatment of various diseases. In the context of the present invention, treatment includes the therapy as well as the prophylaxis of the respective diseases.

Examples of diseases which can be treated with the compound (I) according to the present invention include cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothelial damage after PTCA, hypertension including essential hypertension, pulmonary hypertension, and secondary hypertension (renovascular hypertension, chronic glomerulonephritis), erectile dysfunction, ventricular arrhythmia, and the lowering of cardiovascular risk of postmenopausal women or after intake of contraceptives.

Compound (I) can additionally be used in the therapy and prophylaxis of diabetes and diabetes complications (nephropathy, retinopathy), angiogenesis, asthma bronchiale, chronic renal failure, cirrhosis of the liver, osteoporosis, restricted memory performance or a restricted ability to learn.

Preferred indications are stable angina pectoris, coronary heart disease, hypertension, endothelial dysfunction, atherosclerosis and diabetes complications.

The compound according to the formula (I) can also be used in combination with other pharmaceutically active compounds, preferably compounds which are able to enhance the effect of the compound according to the formula (I). Examples of such compounds include: statins; ACE-inhibitors; AT1-antagonists; argininase-inhibitors; PDE V-inhibitors; Ca-antagonists; alpha-blockers; beta-blockers; metimazol and analogous compounds; arginine; tetrahydro-biopterin; vitamins, in particular vitamin C and vitamin B6; niacin.

The compound (I), optionally in combination with other pharmaceutically active compounds, can be administered to animals, preferably to mammals, and in particular to humans, as a pharmaceutical by itself, or in the form of pharmaceutical preparations. Further objects of the present invention are pharmaceutical preparations (or pharmaceutical compositions) which comprise an effective dose of the compound of the formula (I) and a pharmaceutically acceptable carrier, i.e., one or more pharmaceutically acceptable carrier substances and/or additives. Said pharmaceutical preparations are used for stimulating the expression of endothelial NO synthase and in particular a medicament for the therapy and prophylaxis of the above-mentioned syndromes.

The pharmaceutical according to the invention can be administered orally, for example, in the form of pills, tablets, lacquered tablets, sugar-coated tablets, granules, hard and soft gelatin capsules, aqueous, alcoholic or oily solutions, syrups, emulsions or suspensions, or rectally, for example, in the form of suppositories. Administration can also be carried out parenterally, for example, subcutaneously, intramuscularly or intravenously in the form of solutions for injection or infusion. Other suitable administration forms are, for example, percutaneous or topical administration, for example, in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The amount of the compound of the formula (I) in the pharmaceutical preparations normally ranges from 0.2 to 800 mg, preferably from 0.5 to 500 mg, in particular from 1 to 200 mg, per dose, but depending on the type of the pharmaceutical preparation it may also be higher. The pharmaceutical preparations usually comprise 0.5 to 90 percent by weight of the compound of the formula (I). The preparation of the pharmaceutical preparations can be carried out in a manner known per se. To this end, the compound of the formula (I), together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example, maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiological sodium chloride solution, alcohols such as ethanol, glycerol, polyols, sucrose, invert sugar, glucose, mannitol, vegetable oils, etc. It is also possible to lyophilize the compound of the formula (I) and to use the resulting lyophilizates, for example, for preparing preparations for injection or infusion. Suitable carriers for microcapsules, implants or rods are, for example, copolymers of glycolic acid and lactic acid.

Besides the compound (I) and carriers, the pharmaceutical preparations can also contain additives, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula (I) to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the duration of action of the compound (I), on whether the therapy is acute or chronic or prophylactic, or on whether other active compounds are administered in addition to the compound of the formula (I). In general, a daily dose of approximately 0.01 to 100 mg/kg, preferably 0.1 to 10 mg/kg, in particular 0.3 to 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compound according to the formula (I) can also be used for purposes other than those indicated in the foregoing. Non-limiting examples include diagnostic purposes, the use as biochemical tools, and as intermediates for the preparation of further compounds, e.g. pharmaceutically active compounds.

The present invention will now be illustrated in the following example:

EXAMPLE

Preparation of 4-Fluoro-N-(indan-2-yl)-benzamide 43.70 g (258 mol) 2-aminoindane hydrochloride and 53.43 g (528 mmol) triethylamine were mixed with 250 ml of tetrahydrofuran, 42.89 g (270 mmol) 4-fluorobenzoylchloride were added, and the mixture was stirred for 2 h at RT.

The resulting mixture was then poured onto an ice/HCl-mixture, the obtained precipitate was filtered, washed with a NaHCO$_3$-solution and water and dried in vacuo. The crude product was crystallized from methanol. There were obtained 47.8 g (73%) of a white, crystalline product.

mp.:167° C.

MS: M+H$^+$:256.1

$^1$H-NMR (300 MHz, d$_6$-DMSO): 2.96 (dd, 2H, H1/H3), 3.25 (dd, 2H, H3/H1), 4.70 (sextett, 1H, H2), 7.12–7.19 (m, 2H, H4,7/5,6), 7.20–7.28 (m, 2H, H5,6/4,7), 7.30 (t, 2H, H3', 5'), 7.95 (dd, 2H, H2',6'), 8.68 (d, 1H, NH)

Measurement of Activation of eNOS Transcription

Activation of eNOS transcription was measured as described in detail in Li et al. "Activation of protein kinase C alpha and/or epsilon enhances transcription of the human endothelial nitric oxide synthase gene", Mol. Pharmacol. 1998, 53: 630–637.

Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with the compound (I).

Prior to incubation of the cells, the compound (I) was dissolved in sterile DMSO. A final concentration of 0.5% DMSO in complete medium was obtained. Induction of reporter gene expression in these cells was measured using a standard luciferase assay system (Promega, Cat. No E150) according to the manufacturer's instructions. Luciferase induction in cells incubated with compound (I) were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. EC$_{50}$ values of transcription induction ratios as a function of compound concentration were determined graphically.

The effect of the compound (I) on eNOS-transcription was confirmed in a second assay based on eNOS protein detection. Primary human umbilical vein cord endothelial cells (HUVEC) were isolated and cultivated according to standard procedures. Confluent cells were incubated with compound (I) for 18 h and the effect on eNOS protein expression determined by a quantitative Western blotting procedure. After incubation of compound (I), HUVEC were lysed in ice-cold lysis buffer containing 10 mM Tris-HCl, pH 8.0, 1% SDS and protease inhibitors. The lysate was subjected to a standard denaturating polyacrylamid gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

For the compound (I), the $EC_{50}$-value was 0.8 µM, the TIR(max)–value was 4.10.

Animal Models

All animal experiments were performed in accordance to the German animal protection law and to the guidelines for the use of experimental animals as given by the Guide for the Care and Use of Laboratory Animals of the US National Institutes of Health.

Animals and Treatment (Experiments A-C)

ApoE and eNOS deficient mice (C57BL/6J background, Jackson Laboratory, Bar Harbor, Me.) were used. All animals were 10–12 weeks of age and weighed 22 to 28 g. Three days before surgery, mice were divided into 4 groups (apoE control, n=10–12; apoE with compound (I), n=10–12; eNOS control, n=10–12; eNOS with compound (I), n=10–12) and received either a standard rodent chow (containing 4% fat and 0,001% cholesterol; in the following designated as placebo group) or a standard rodent chow+ compound (I) (10 or 30 mg/kg/d p.o.).

A Anti-hypertensive Effect in ApoE Knockout Mice

Blood-pressure was determined in conscious mice using a computerized tail-cuff system.

For compound (I), after 4 months treatment of ApoE deficient mice blood pressure was significantly (p<0.05) lowered in the 30 mg/kg/d group compared to placebo treatment (92±5 mmHg versus 115±2 mmHg). No blood pressure reduction could be observed at similar dosing in eNOS deficient mice after 4 weeks treatment.

B Inhibition of Neointima Formation and Atherogenesis (Femoral Artery Cuff)

After 3 days treatment of ApoE deficient mice with compound (I), (10 mg/kg/d pressed in chow), animals were anesthetized with an intraperitoneal injection of pentobarbital (60 mg/kg) followed by an intramuscular injection of xylazin (2 mg/kg) and a cuff was placed around the femoral artery as described in Moroi et at. (J Clin Invest. 101:1225–32, 1998). Briefly, the left femoral artery was dissected. A non-occlusive 2.0 mm polyethylene cuff made of PE-50 tubing (inner diameter 0.56 mm, outer diameter 0.965 mm, Becton Dickinson, Mountain View, Calif.) was placed around the artery and tied in place with two 7-0 sutures. The right femoral artery was isolated from the surrounding tissues but a cuff was not placed. Treatment with compound (I) was continued for 14 days after surgery. Then the animals were sacrificed. The aortas were taken for determination of vascular eNOS expressions by quantitative western blotting. Both femoral arteries were harvested, fixed in formalin and embedded in paraffin. 20 cross sections (10 µm) were cut from the cuffed portion of the left femoral artery and from the corresponding segment of the right artery. Sections were subjected to standard hematoxylin and eosin staining. Morphometric analyses were performed using an image analysis computer program (LeicaQWin, Leica Imaging Systems, Cambridge, GB). For each cross section the area of the lumen, the neointima and the media were determined. To this end, the neointima was defined as the area between the lumen and the internal elastic lamina and the media was defined as the area between the internal and the external elastic lamina. The ratio between the area of the neointima and the area of the media was expressed as the neointima/media ratio.

Compound (I) reduced the maladaptive neo-intima formation by a factor of 2, decreasing the neointima to media ratio from 0.39±0.07 in the placebo group to 0.170±0.04 in the compound group. In parallel, vascular eNOS expression was enhanced by a factor of 2.1. No effect of compound (I) could be demonstrated in a similar setup using eNOS deficient mice instead of ApoE knockout mice.

C Prevention of Atherosclerotic Plaque Formation in Chronic Treatment

ApoE deficient mice were treated for 16 weeks with compound (I) pressed in chow and finally sacrificed. Aortas were removed from each mouse, fixed in formalin and embedded in paraffin. Plaque formation was measured via lipid lesions formation in the aortas (from aortic arch to diaphragm) and was analyzed by oil red O staining. For quantifying the effect of the respective compound on vascular eNOS expression the femoral arteries were used in this experiment.

Compound (I) according to the present invention significantly reduced plaque formation (5.2±1% versus 13.3±2.6 in the placebo group, values in overall plaque size in % of total surface). Vascular eNOS expression was found to be 1.75 fold up-regulated in the treatment group.

D Improvement of Coronary Function in Diseased ApoE Deficient Mice

Old Male wild-type C57BL/6J mice (Charles River Wiga GmbH, Sulzfeld), and apolE deficient mice (C57BL/6J background, Jackson Laboratory, Bar Harbor, Me.) 6 month of age and weighing 28 to 36 g were used in the experiments. Mice were divided into 3 groups (C57BL/6, n=8; apoE control, n=8; apoE with compound (I), n=8) and received for 8 weeks either a standard rodent chow (containing 4% fat and 0,001% cholesterol) or a standard rodent chow+ compound (I) (30 mg/kg/d p.o.).

Mice were anesthetized with sodium pentobarbitone (100 mg/kg i.p.), and the hearts were rapidly excised and placed into ice-cold perfusion buffer. The aorta was cannulated and connected to a perfusion apparatus (HUGO SACHS ELECTRONICS, Freiburg, Germany) which was started immediately at a constant perfusion pressure of 60 mm Hg. Hearts were perfused in a retrograde fashion with modified Krebs bicarbonate buffer, equilibrated with 95% $O_2$ and 5% $CO_2$ and maintained at 37.5° C.

A beveled small tube (PE 50) was passed through a pulmonary vein into the left ventricle and pulled through the ventricular wall, anchored in the apex by a fluted end, and connected to a tip-micromanometer (Millar 1.4 French). The left atrium was cannulated through the same pulmonary vein and the heart switched to the working mode with a constant preload pressure of 10 mm Hg and an afterload pressure of 60 mm Hg. Aortic outflow and atrial inflow were continuously measured using ultrasonic flow probes (HSE/ Transonic Systems Inc.). Coronary flow was calculated as the difference between atrial flow and aortic flow. All hemodynamic data were digitized at a sampling rate of 1000•Hz and recorded with a PC using specialized software (HEM, Notocord).

Hearts were allowed to stabilize for 30 min. All functional hemodynamnic data were measured during steady state, and during volume- and pressure loading.

Left ventricular function curves were constructed by varying pre-load pressure. For acquisition of preload curves, afterload was set at 60 mm Hg and preload was adjusted in 5 mm Hg steps over a range of 5 to 25 mm Hg. Hearts were allowed to stabilize at baseline conditions between pressure- and volume-loading.

Isolated hearts from ApoE deficient animals displayed a lower coronary flow in this setup compared to C57B16 wildtype mice (3.6 ml/min versus 4.95 ml/min). Treatment of ApoE deficient animals with the compound (I) according to the present invention increased coronary flow to 5 ml/min comparable to the levels of non-diseased wildtype mice. Compound (I) also improved pre-load dependent coronary flow and reduced the incidence of ventricular arrhythmias as an indicator for anti-ischemic efficacy.

We claim:

1. A method for treating a cardiovascular disease in a mammal suffering therefrom, which method comprises administering a physiologically active amount of 4-fluoro-N-indan-2-yl benzamide according to the formula (I)

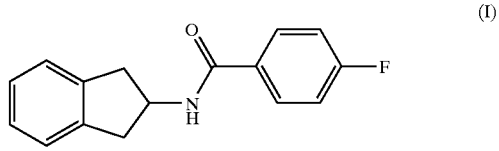

to the mammal.

2. The method according to claim 1, wherein the mammal is a human.

3. A method for treating a mammal a disease chosen from unstable angina pectoris, acute coronary syndrome, heart failure, myocardial infarction, thrombosis, peripheral artery occlusive disease, restenosis, and endothelial damage after PTCA in a mammal suffering therefrom, which method comprises administering a physiologically active amount of 4-fluoro-N-indan-2-yl benzamide according to the formula (I)

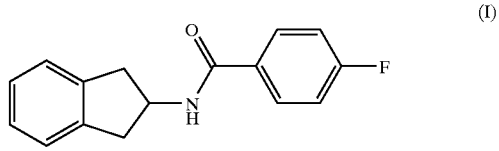

to the mammal.

4. The method according to claim 3, wherein the mammal is a human.

5. A method for treating a cardiovascular disease in a mammal suffering therefrom, which method comprises administering a pharmaceutical preparation comprising an effective amount of 4-fluoro-N-indan-2-yl benzamide according to the formula (I)

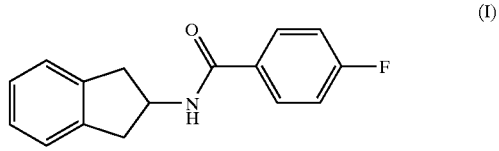

and a pharmaceutically acceptable carrier to the mammal.

6. The method according to claim 5, wherein the mammal is a human.

7. The method according to claim 5, wherein the pharmaceutical preparation is in the form of a pill, tablet, granule, hard or soft gelatin capsule, aqueous, alcoholic or oily solution, syrup, emulsion or suspension, suppository, solution for injection or infusion, ointment, tincture, spray, transdermal therapeutic system, nasal spray, aerosol mixture, microcapsule, implant or rod.

8. The method according to claim 7, wherein the tablet is chosen from a lacquered tablet and a sugar-coated tablet.

9. A method for treating a disease chosen from unstable angina pectoris, acute coronary syndrome, heart failure, myocardial infarction, thrombosis, peripheral artery occlusive disease, restenosis, and endothelial damage after PTCA in a mammal suffering therefrom, which method comprises administering a pharmaceutical preparation comprising an effective amount of 4-fluoro-N-indan-2-yl benzamide according to the formula (I)

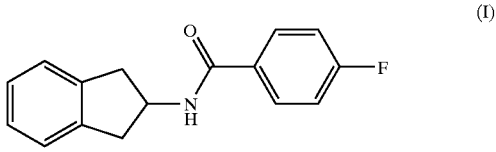

and a pharmaceutically acceptable carrier to the mammal.

10. The method according to claim 9, wherein the mammal is a human.

11. The method according to claim 10, wherein the pharmaceutical preparation is in the form of a pill, tablet, granule, hard or soft gelatin capsule, aqueous, alcoholic or oily solution, syrup, emulsion or suspension, suppository, solution for injection or infusion, ointment, tincture, spray, transdermal therapeutic system, nasal spray, aerosol mixture, microcapsule, implant or rod.

12. The method according to claim 11, wherein the tablet is chosen from a lacquered tablet and a sugar-coated tablet.

13. A method for treating erectile dysfunction or osteoporosis in a mammal suffering therefrom, which method comprises administering a physiologically active amount of 4-fluoro-N-indan-2-yl benzamide according to the formula (I)

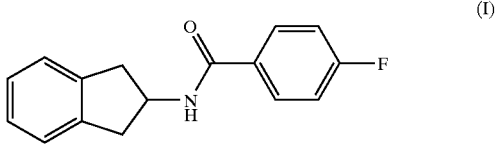

to the mammal.

14. The method according to claim 13, wherein the mammal is a human.

15. A method for treating erectile dysfunction or osteoporosis in a mammal suffering therefrom, which method comprises administering a pharmaceutical preparation comprising an effective amount of 4-fluoro-N-indan-2-yl benzamide according to the formula (I)

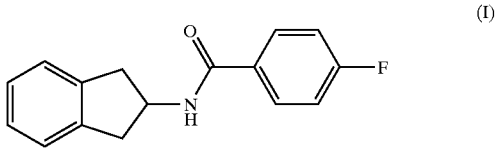

and a pharmaceutically acceptable carrier to the mammal.

16. The method according to claim 15, wherein the mammal is a human.

17. The method according to claim 15, wherein the pharmaceutical preparation is in the form of a pill, tablet, granule, hard or soft gelatin capsule, aqueous, alcoholic or oily solution, syrup, emulsion or suspension, suppository, solution for injection or infusion, ointment, tincture, spray, transdermal therapeutic system, nasal spray, aerosol mixture, microcapsule, implant or rod.

18. The method according to claim 17, wherein the tablet is chosen from a lacquered tablet and a sugar-coated tablet.

* * * * *

UNITED STATES PATENT AND TRADEMARK OFFICE
CERTIFICATE OF CORRECTION

PATENT NO. : 6,812,253 B2
DATED : November 2, 2004
INVENTOR(S) : Paulus Wohlfart et al.

It is certified that error appears in the above-identified patent and that said Letters Patent is hereby corrected as shown below:

Column 9,
Line 18, "treating a mammal a" should read -- treating a --.

Column 10,
Line 15, "claim 10," should read -- claim 9, --.

Signed and Sealed this

First Day of March, 2005

JON W. DUDAS
*Director of the United States Patent and Trademark Office*